US012806130B2

(12) United States Patent
He et al.

(10) Patent No.: US 12,806,130 B2
(45) Date of Patent: Nov. 24, 2026

(54) COLOR-CHANGING DENTIFRICE COMPOSITIONS

(71) Applicant: The Procter & Gamble Company, Cincinnati, OH (US)

(72) Inventors: Cuijiao He, Beijing (CN); Hanjiang Zhu, Beijing (CN); Feifei Ai, Beijing (CN); Lifeng Zhao, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 443 days.

(21) Appl. No.: 18/327,181

(22) Filed: Jun. 1, 2023

(65) Prior Publication Data

US 2023/0398052 A1 Dec. 14, 2023

(51) Int. Cl.

| | |
|---|---|
| ***A61K 8/73*** | (2006.01) |
| ***A61K 8/84*** | (2006.01) |
| ***A61Q 11/02*** | (2006.01) |

(52) U.S. Cl.

CPC ................ *A61K 8/731* (2013.01); *A61K 8/84* (2013.01); *A61Q 11/02* (2013.01); *A61K 2800/43* (2013.01); *A61K 2800/56* (2013.01)

(58) Field of Classification Search

CPC . A61K 8/11; A61K 8/731; A61K 8/84; A61K 8/8129; A61K 2800/43; A61K 2800/56; A61Q 11/02; A61Q 11/00

See application file for complete search history.

(56) References Cited

U.S. PATENT DOCUMENTS

| | | | | |
|---|---|---|---|---|
| 4,348,378 A | | 9/1982 | Kosti | |
| 4,515,769 A | * | 5/1985 | Merritt | A23G 4/043 426/534 |

FOREIGN PATENT DOCUMENTS

| | | | | |
|---|---|---|---|---|
| KR | 20100085344 A | * 7/2010 | | A61K 8/73 |
| LR | 20100085344 A | * 7/2010 | | |
| WO | WO-2007012981 A2 | * 2/2007 | | A23P 10/30 |
| WO | WO-2011006657 A1 | * 1/2011 | | C11D 9/444 |
| WO | 2012082098 A1 | 6/2012 | | |
| WO | 2019081325 A1 | 5/2019 | | |

OTHER PUBLICATIONS

PCT Search Report and Opinion for PCT/CN2022/098008 dated Nov. 24, 2022; 13 pages.

* cited by examiner

*Primary Examiner* — Lezah Roberts

(74) *Attorney, Agent, or Firm* — John G. Powell; Elizabeth A. Conklin

(57) ABSTRACT

A color-changing oral care composition, in particular a dentifrice composition, contains: (i) an encapsulated dye particle comprising a dye and a coating layer encapsulating the dye, where the coating layer comprising hydroxy propyl methyl cellulose (HPMC) and polyvinyl alcohol (PVA), and (ii) 0.2% to 1.2% by weight of the composition, of flavor ingredients, where the flavor ingredients have a clog P value of 2 to 6, and where the flavor ingredients have Hansen Solubility Parameter (HSP) Distance (Ra) with hydroxy propyl methyl cellulose (HPMC) greater than 7.5, and Hansen Solubility Parameter (HSP) Distance (Ra) with polyvinyl alcohol (PVA) greater than 3.5.

10 Claims, No Drawings

COLOR-CHANGING DENTIFRICE COMPOSITIONS

FIELD OF THE INVENTION

The present invention relates to a color-changing dentifrice composition, and the method of using the same.

BACKGROUND OF THE INVENTION

As brushing teeth is generally considered a mundane routine of everyday life, consumers desire more delightful visual stimuli during the brushing experience. For example, visible color change during brushing after a period of time will provide a clear signal to indicate when the user has brushed for a suitable amount of time. Thus, a color-changing dentifrice will provide the user not only a visual cue to make sure adequate brushing time, but also a sensory entertainment. The need is especially among parents who want to make sure the children brush enough time. Encapsulated dye or pigment may be used to provide color-changing where the dye or pigment is released out of the encapsule after brushing a certain of time. However, there is a challenge for the dentifrice composition containing such encapsulated dye or pigment is leakage of the dye and unexpected appearance change on shelf. Therefore, there is a continuous need for a dentifrice with color-changing characteristics while at the same time, providing satisfied or improved stability, especially after a relatively long shipping or shelf time.

SUMMARY OF THE INVENTION

Surprisingly, the applicant discovers a dentifrice composition which maintains desired appearance with no color leakage even after a long shelf-time or shipping time, and also provide color-changing benefit during teeth-brushing. Particularly, the dentifrice composition exhibits one color in appearance when in the tube, even for a long shelf time. Once upon usage, it exhibits a color-changing (e.g., from white to blue, or from pink to purple, etc.) after brushing for a certain period of time. The dentifrice composition of the present invention comprises an encapsulated dye particle and a flavor system characterized by a particular ClogP Value and Hansen Solubility Parameter (HSP) Distance (Ra).

An advantage of the present invention is to provide a dentifrice composition that introduces color change upon usage after a certain period of time, so as to provide signal cue that a user has brushed adequate time.

Another advantage of the present invention is to provide a dentifrice having stable attractive appearance before usage, and a unique color-changing sensorial experience during usage.

Still another advantage of the present invention is to provide a phase stable formulation.

One aspect of the invention provides for a color-changing dentifrice composition, comprises:

i) from 0.1% to 4%, by weight of the composition, of an encapsulated dye particle comprising a dye and a coating layer encapsulating the dye, wherein the coating layer comprises at least hydroxy propyl methyl cellulose (HPMC) and polyvinyl alcohol (PVA), and ii) 0.2% to 1.2% by weight of the composition, of flavor ingredients, wherein the flavor ingredients have a clog P value of 2 to 6, and wherein the flavor ingredients have Hansen Solubility Parameter (HSP) Distance (Ra) with hydroxy propyl methyl cellulose (HPMC) greater than 7.5, and Hansen Solubility Parameter (HSP) Distance (Ra) with polyvinyl alcohol (PVA) greater than 3.5. Preferably, the flavor ingredients are selected from those having a Molecular Weight from 120 to 400, preferably from 150 to 400.

Preferably, the dentifrice composition of the present invention exhibits a color-changing after a period of 30 to 90 seconds upon usage.

Another aspect of the invention provides a method of use comprising the step of brushing teeth with a composition of the present invention.

These and other features, aspects, and advantages of the present invention will become evident to those skilled in the art from the detailed description which follows.

DETAILED DESCRIPTION OF THE INVENTION

Definitions

As used herein, the articles including "a" and "an" when used in a claim, are understood to mean one or more of what is claimed or described.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "substantially free" as used herein refers to no intentional amount of that material is added to the composition or an amount of a material that is less than 0.05%, 0.01%, or 0.001% of the composition. The term "essentially free" as used herein means that the indicated material is not deliberately added to the composition, or preferably not present at analytically detectable levels. It is meant to include compositions whereby the indicated material is present only as an impurity of one of the other materials deliberately added. The term "free" as used herein refers to no reasonably detectable amount of that material is present in the composition.

The term "dentifrice" as used herein means paste, gel, powder, tablets, or liquid formulations, unless otherwise specified, that are used to clean the surfaces of the oral cavity. Preferably the dentifrice compositions of the present invention are single phase compositions. One example of a dentifrice is toothpaste (for brushing teeth). The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

The Dentifrice Composition

The dentifrice composition of the present invention is a color-changing dentifrice composition. The color-changing dentifrice composition comprises an encapsulated dye particle, where when brushing continues the encapsulated dye particle disintegrates and provides color signal or a color change.

The color-changing dentifrice composition comprises: i) from 0.1% to 4%, by weight of the composition, of an encapsulated dye particle comprising a dye and a coating layer encapsulating the dye, wherein the coating layer comprises at least hydroxy propyl methyl cellulose (HPMC) and polyvinyl alcohol (PVA), and ii) 0.2% to 1.2% by weight of the composition, of flavor ingredients, wherein the flavor ingredients have a clog P value of 2 to 6, and wherein the flavor ingredients have Hansen Solubility Parameter (HSP) Distance (Ra) with hydroxy propyl methyl cellulose (HPMC) greater than 7.5, and Hansen Solubility Parameter (HSP) Distance (Ra) with polyvinyl alcohol (PVA) greater than 3.5.

In particular, the color-changing dentifrice composition comprises an encapsulated dye particle. The encapsulated dye particle is present at a level of from 0.1% to 4%, by weight of the composition, more preferably from 0.15% to 3.75%, alternatively from 0.2% to 3.5%, or from 0.3% to 3.2%. The encapsulated dye particle comprises a dye and a coating layer encapsulating the dye. The weight ratio of the dye and the coating layer can be from 1:99 to 99:1. For example, the encapsulated dye particle comprises from 0.01% to 40%, by weight of the particle, of the dye, preferably from 0.1% to 35%, alternatively from 0.5% to 30%, or 1% to 25%, or 5% to 20% by weight of the particle.

Preferably, Suitable dye used in the encapsulated dye particle include dyes, dye lakes, dye-clay conjugates, and optionally organic and inorganic pigments. Suitable dyes include small molecule dyes and polymeric dyes. Suitable small molecule dyes include dyes selected from the classes of direct, basic, reactive, or hydrolyzed reactive, solvent, or disperse dyes classified under the color Index (C.I.) and individually or in combination providing the desired hue, for example, as blue, violet, red, green, or black. In another aspect, suitable small molecule dyes include the following numbered small molecule dyes selected from the dye index (Society of Dyers and Colourists, Bradford, UK): direct violet dyes such as 9, 35, 48, 51, 66 and 99, direct blue dyes such as 1, 71, 80 and 279, acid red dyes such as 17, 73, 52, 88 and 150, acid violet dyes such as 15, 17, 24, 43, 49 and 50, acid blue dyes such as 15, 17, 25, 29, 40, 45, 75, 80, 83, 90 and 113, acid black dyes such as 1, basic violet dyes such as 1, 3, 4, 10 and 35, basic blue dyes such as 3, 16, 22, 47, 66, 75 and 159, disperse or solvent dyes such as those described in EP1794275 or EP1794276, or dyes as disclosed in U.S. Pat. No. 7,208,459B2, and mixtures thereof. In another aspect, suitable small molecule dyes include those selected from the following color index numbers: acid violet 17, direct blue 71, direct violet 51, direct blue 1, acid red 88, acid red 150, acid blue 29, acid blue 113, or mixtures thereof. In alternative examples, suitable dye includes without limitation those dyes approved by appropriate regulatory bodies such as the FDA and those listed in the European Food and Pharmaceutical Directives and include colors such as FD&C and D&C dyes. Specific examples of dyes include: FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof.

Preferably, the encapsulated dye particle comprises from 1% to 99%, preferably from 5% to 95%, more preferably from 10% to 90%, of coating layer, by weight of the encapsuled dye particle. Preferably, the coating layer comprises a binder, a filler, and optionally a disintegrant. Preferably, the coating layer comprises a binder which is selected from either hydroxy propyl methyl cellulose (HPMC), or polyvinyl alcohol (PVA), or preferably both of HPMC and PVA.

Optionally, the coating layer may further include other binders selected from polymer materials such as carboxymethylcellulose, methylcellulose, crosslinked polyvidone, sodium alginate, xanthan gum, and agar. Suitable filler contained in the coating layer of the encapsulated dye particle may include edible, soluble material comprising glucose, mannitol, sorbitol, fructose, or lactose, or any combinations thereof.

In an example, the encapsulated dye particle in the color-changing dentifrice composition comprises 0.1% to 30% of a dye, 0.1% to 15% of a binder, 1% to 80% a filler, 0.1% to 5% of disintegrant.

The color-changing dentifrice composition of the present invention further comprises from 0.2% to 1.2% by weight of the composition, of flavor ingredients. The flavor ingredients are characterized as having a Clog P value of 2-6, as well as having Hansen Solubility Parameter (HSP) Distance (Ra) with hydroxy propyl methyl cellulose (HPMC) greater than 7.5, and Hansen Solubility Parameter (HSP) Distance (Ra) with polyvinyl alcohol (PVA) greater than 3.5.

Hansen Solubility Parameter (HSP) Distance (Ra) can be calculated by HSP parameters of the flavor ingredients and the polymer, with the equation below:

$$Ra^2=4(\delta D1-\delta D2)^2+(\delta P1-\delta P2)^2+(\delta H1-\delta H2)^2$$

Where,

δD1 is Dispersion factor of flavor ingredient, δD2 is Dispersion factor of the polymer (e.g., HPMC or PVA).

δP1 is Polar factor of flavor ingredient, δP2 is Polar factor of the polymer (e.g., HPMC or PVA).

δH1 is Hydrogen bond factor of flavor ingredient, δH2 is Hydrogen bond factor of the polymer (e.g., HPMC or PVA).

Preferably, the flavor ingredients present in the color-changing dentifrice composition have Molecular Weight from 120 to 400, preferably from 150 to 400. For example, the flavor ingredients can be selected from the group consisting of Thymol, Menthol, Caprylic/capric triglyceride, Carvone, Menthone, g-Undecalactone, or combinations thereof.

Table 1 below lists HSP Ra value of some examples of suitable flavor ingredients for the present invention.

TABLE 1

| Flavor ingredients | Clog P | δD | δH | δP | Ra with HPMC | Ra with PVA |
|---|---|---|---|---|---|---|
| Thymol | 3.08 | 16.5 | 6.9 | 3.5 | 8.9 | 3.9 |
| Menthol | 2.91 | 16.5 | 6.9 | 3.5 | 8.9 | 3.9 |
| Caprylic triglyceride | 3.97 | 16.3 | 7.4 | 4.1 | 8.5 | 4.7 |
| Carvone | 2.80 | 17.5 | 3.7 | 5.8 | 9.2 | 3.6 |
| Menthone | 3.16 | 16.9 | 2.4 | 5 | 11.1 | 3.5 |
| g-Undecalactone | 3.18 | 16.4 | 4.2 | 9.2 | 9.0 | 7.4 |

Without limiting to bound by any theory, the above-mentioned characteristics of the flavor ingredients surprisingly provide a compatible and stable system with the encapsulated dye particle in the dentifrice composition.

Preferably, the color-changing dentifrice composition comprises encapsulated dye particle, wherein the encapsulated dye particle has an average particle size of from 100 microns to 2000 microns, preferably from 150 to 1500 microns. For example, the encapsulated dye particle has an average particle size of from 200 microns to 1800 microns, or from 250 microns to 1600 microns.

The encapsulated dye particle can be produced by any suitable method for making particles, including but not limited to fluidized bed granulation, agglomeration, protrusion, etc.

The color-changing dentifrice composition of the present invention further comprises active ingredients selected from fluoride ion source, metal ion source such as stannous ion source, zinc ion source, as well as further comprises one or more ingredients selected from the group consisting of orally acceptable carriers, abrasives, binders, humectant, surfactant, and combinations thereof.

Fluoride Ion Source

Optionally, but preferably, the dentifrice compositions may comprise an effective amount of a fluoride ion source. The fluoride ion may be present in an amount sufficient to give a fluoride ion concentration in the composition at 25° C., and/or in one embodiment can be used at levels of from about 0.0025% to about 5%, preferably from 0.01% to 0.5%, more preferably from 0.02% to by weight of the composition. Examples of fluoride ion sources include stannous fluoride, sodium fluoride, potassium fluoride, amine fluoride, sodium monofluorophosphate, and zinc fluoride.

The method for assessing soluble fluoride is described consistent with the China's National Standard Method GB8372-2008. Briefly, an ion-selective electrode (ISE) is used to test soluble fluoride in dentifrice. An example of a fluoride ion meter is SARTORIUS PP-50, but an equivalent may be used.

Surfactants

The dentifrice composition can comprise one or more surfactants. The surfactants can be used to make the compositions more cosmetically and/or consumer acceptable. The surfactant can be a detersive material which imparts to the composition detersive and foaming properties. Suitable surfactants include anionic, cationic, nonionic, zwitterionic, amphoteric and/or betaine surfactants. Other suitable surfactants include sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Sodium lauryl sulfate is a preferred surfactant. The dentifrice composition can comprise one or more surfactants each at a level from about 0.01% to about 15%, from about 0.3% to about 10%, or from about 0.3% to about 2.5%, by weight of the dentifrice composition.

Thickening Agent

The dentifrice composition can comprise one or more thickening agents. Thickening agents can be useful in the dentifrice compositions to provide a gelatinous structure that stabilizes the toothpaste against phase separation. Suitable thickening agents include polysaccharides, polymers, and/or silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the dentifrice composition as well as various ranges of average molecular ranges. The polymer can comprise polyacrylate crosspolymer, such as polyacrylate crosspolymer-6. Suitable sources of polyacrylate crosspolymer-6 can include Sepimax Zen™ commercially available from Seppic.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The dentifrice composition can comprise from 0.01% to about 15%, from 0.1% to about 10%, from about 0.2% to about 5%, or from about 0.5% to about 2% of one or more thickening agents.

Abrasive

The dentifrice composition of the present invention can comprise abrasive. Abrasives can be added to dentifrice formulations to help remove surface stains from teeth. The abrasive can comprise calcium abrasive and/or silica abrasive.

The calcium abrasive can be any suitable abrasive compound that can provide calcium ions in a dentifrice composition and/or deliver calcium ions to the oral cavity when the dentifrice composition is applied to the oral cavity. The dentifrice composition can comprise from about 5% to about 70%, from about 10% to about 60%, from about 20% to about 50%, from about 25% to about 40%, or from about 1% to about 50% of a calcium abrasive. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The dentifrice composition can also comprise silica abrasive, such as silica gel (by itself, and of any structure), precipitated silica, amorphous precipitated silica (by itself, and of any structure as well), hydrated silica, and/or combinations thereof. The dentifrice composition can comprise from about 5% to about 70%, from about 10% to about 60%, from about 10% to about 50%, from about 20% to about 50%, from about 25% to about 40%, or from about 1% to about 50% of a silica abrasive.

The abrasive can also comprise bentonite, perlite, titanium dioxide, alumina, hydrated alumina, calcined alumina, aluminum silicate, insoluble sodium metaphosphate, insoluble potassium metaphosphate, insoluble magnesium carbonate, zirconium silicate, particulate thermosetting resins and/or other suitable abrasive materials. The dentifrice composition can comprise from about 5% to about 70%, from about 10% to about 60%, from about 10% to about 50%, from about 20% to about 50%, from about 25% to about 40%, or from about 1% to about 50% of another abrasive.

Other Active Agents

The dentifrice compositions of the present invention may optionally also include other anti-bacterial agents, preferably present in an amount of from 0.035% or more, from 0.05% to 2%, from to 1%, by weight of the composition. Examples of these other anti-bacterial agents may include non-cationic anti-bacterial agents such as, for example, halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilidies. Other useful anti-bacterial agents are enzymes, including endoglycosidase, papain, dextranase, mutanase, and combinations thereof.

pH

The pH of the dentifrice compositions as described herein can be from about 4 to about 10, from about 6 to about 8, alternatively from 4.5 to 7.5. The pH of the dentifrice compositions, as described herein, can also be at least about 6, at least about 6.5, or at least about 7. The pH of a mouth rinse solution can be determined as the pH of the neat solution. The pH of a dentifrice composition can be determined as a slurry pH, which is the pH of a mixture of the dentifrice composition and water, such as a 1:4, 1:3, or 1:2 mixture of the dentifrice composition and water. The pH of the dentifrice compositions as described herein have a preferred pH of from about 4 to about 10, from about 5 to about 9, from about 6 to 8, or about 7.

Water

In a low water dentifrice formulation, the dentifrice composition comprises from about 10% to about 45%, by weight of the composition, of water. The low water dentifrice composition can comprise from about 10% to about 35%, from about 15% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than about 5%, less than about 1%, or 0%, by weight of the composition, of water. The water may be added to the anhydrous formulation and/or may come into the dentifrice composition from the inclusion of other ingredients.

Humectant

The dentifrice composition can comprise one or more humectants, have low levels of humectant, be free of humectant, be substantially free of humectant, and/or essentially free of humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The dentifrice composition can comprise one or more humectants each at a level of from 0 to about 70%, from about 5% to about 50%, from about 10% to about 60%, or from about 20% to about 80%, by weight of the dentifrice composition.

Colorant

The dentifrice composition may comprise colorants which selected from pigments, pealing agents, filler powders, talc, mica, titanium dioxide, dye lakes, magnesium carbonate, calcium carbonate, bismuth oxychloride, zinc oxide, and combinations thereof. One preferred example is titanium dioxide ($TiO_2$). Titanium dioxide is a white powder which provides opacity (thus possible provide color comparison in a transparent/translucent paste) to the composition. The colorant present in the particle may be a mixture of at least two ingredients selected from the group consisting of pigments, pealing agents, filler powders, talc, mica, titanium dioxide, dye lakes, magnesium carbonate, calcium carbonate, bismuth oxychloride, zinc oxide, and combinations thereof.

Method of Use

The present invention also relates to methods for treating the oral cavity comprising administering to the oral care cavity a dentifrice composition according to the present invention. In an embodiment, the term "treating" refers to cleaning and polishing teeth. The method of use herein comprises contacting a subject's dental enamel surfaces and oral mucosa with the oral care compositions according to the present invention. The method of treatment may be by brushing with a dentifrice or rinsing with a dentifrice slurry or mouth rinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral care composition may be used as frequently as toothpaste, or may be used less often, for example, weekly, or used by a professional in the form of a prophy paste or other intensive treatment.

The invention further provides a method of cleaning the teeth comprising brushing with a dentifrice composition according to the present invention, wherein brushing is continued until the encapsulated dye particle disintegrates and the dye provides a color signal to the user of adequate brushing, for example, wherein the brushing time before the dye particle dissolves is between 30 and 180 seconds, e.g., about 45-60 seconds for a toothpaste for use by a child and about 90-120 seconds for a toothpaste for use by an adult.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Examples Preparation

A toothpaste base formula is prepared by admixture of the components in below Table 2, with amounts of components in wt %, in the proportions indicated.

TABLE 2

Toothpaste Base formula Example (without Flavor)

| Ingredients | Base Formula (% by weight) |
|---|---|
| Water | 5-10 |
| Sorbitol Solution | 50-75 |
| Na-Saccharin | 0.2-0.3 |
| Fluoride ion source | 0.2-0.7 |
| Phosphate buffer | 0.5-1.5 |
| Binder polymer | 0.5-1.5 |
| Silica abrasive | 10-20 |
| SLSS | 3-5 |
| Encapsulated Dye particle* | 0.5-2 |
| Total | 98.0 |
| pH | 6.7~7.5 |

*The encapsulated dye particle is commercially available from Chongqing Pellets Biotech Co., Ltd. Under tradename AC-AZR50-305, containing 1-5% of CI73360, 1-5% of hydroxypropyl methyl cellulose, 1-5% of PVA, and 20-30% titanium dioxide, 40-50% of mannitol.

Inventive Examples 1 to 3 and Comparative Examples A to C are all prepared based on the toothpaste base formula (Table 2), the differences are the components of the flavor showing in Table 3 below with amounts of components in wt %. The samples may be suitably prepared by conventional methods chosen by the formulator. The level of flavor ingredients is weight percentage in the final toothpaste samples. Inventive Examples 1 to 3 are inventive formulations according to the present invention, and Comparative Examples A to C are formulated for comparative purpose. The comparative examples contain flavor out of the scope of the present invention (either level or physics properties such as clogP).

TABLE 3

Toothpaste Composition Examples (with Flavor)

| Ingredients (by weight/%) | Comparative Example A | Comparative Example B | Comparative Example C | Inventive Example 1 | Inventive Example 2 | Inventive Example 3 |
|---|---|---|---|---|---|---|
| Toothpaste Base | 98.0 | 98.0 | 98.0 | 98.0 | 98.0 | 98.0 |
| Flavor X[1] | 0.15 | 0.14 | 0.14 | 0.49 | 0.39 | 0.14 |
| Flavor Y[2] | 0 | 0 | 0 | 0 | 0 | 0.45 |
| Flavor Z[3] | 0 | 0.12 | 0.45 | 0 | 0.12 | 0 |
| FLV accord | 0.600 | 0.600 | 0.600 | 0.600 | 0.600 | 0.600 |
| Sorbitol Solution & Minors | Q.S. | Q.S. | Q.S. | Q.S. | Q.S. | Q.S. |
| Total | 100.0000 | 100.0000 | 100.0000 | 100.0000 | 100.0000 | 100.0000 |
| pH | 6.7~7.5 | 6.7~7.5 | 6.7~7.5 | 6.7~7.5 | 6.7~7.5 | 6.7~7.5 |

[1]Flavor X is menthol with Clog P value of 2.91

[2]Flavor Y is Caprylic triglyceride (CT) with Clog P value of 3.97

[3]Flavor Z is Isopropyl myristate (IPM) with Clog P value of 7.17

Beads Integrity Grading Method

The toothpaste samples of the Examples in Table 3 are all kept at 40° C. for at least 50 days before being tested by conducting the Beads Integrity Grading method. The method provides a visual assessment regarding the stability of the color beads in a toothpaste formulation.

Each toothpaste sample is squeezed by manual out of the tube onto a sheet of white, unlined paper to form a straight toothpaste ribbon with a minimum length of 10 mm, free of bubbles. The diameter of the toothpaste ribbon should be about the same diameter of the tube orifice and shouldn't be stretched. Visually check the dentifrice sample at a distance approximately 40 cm. A panel of three (3) people visually check if there is broken red beads in the toothpaste ribbon and if red tailings observed. They observe twice for each sample and give a grading. Only both "Pass" for a sample is recorded as "Pass". Photos are also taken for record. The criteria are set as below:

"Pass": No more than 10 broken beads and no more than 5 red tailings caused by broken beads in 10 mm paste.

"Fail": More than 10 broken beads and more than 5 red tailings caused by broken beads in 10 mm paste.

The grading test of the Inventive Examples 1 to 3 and Comparative Examples A to C are measured according to the above-mentioned Beads Integrity Grading Method. Results are shown in Table 4 below.

TABLE 4

Grading results

| Examples | Grading Result |
|---|---|
| Comparative Example A | Fail (3^) |
| Comparative Example B | Fail (3) |
| Comparative Example C | Fail (3) |
| Inventive Example 1 | Pass (3) |
| Inventive Example 2 | Pass (3) |
| Inventive Example 3 | Pass (3) |

^here "3" means 3 votes out of 3 panel users.

It can be seen from Table 4 that the Inventive Examples 1 to 3 exhibit minimum breaking and tailing of the color beads, therefore provide a desired appearance and stability. In the contrary, the Comparative Examples A to C, which contains flavor ingredients out of the scope of the present invention, show undesired appearance results.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A color-changing dentifrice composition, comprising:

i) 0.1% to 4%, by weight of the composition, of an encapsulated dye particle comprising a dye and a coating layer encapsulating the dye, wherein the coating layer comprises 1% to 5% hydroxy propyl methyl cellulose (HPMC), by weight of the encapsulated dye particle and 1% to 5% polyvinyl alcohol (PVA), by weight of the encapsulated dye particle; and ii) 0.2% to 1.2% by weight of the composition, of flavor ingredients, wherein the flavor ingredients have a clog P value of 2 to 6, Hansen Solubility Parameter (HSP) Distance (Ra) with hydroxy propyl methyl cellulose (HPMC) greater than 7.5, and a Hansen Solubility Parameter (HSP) Distance (Ra) with polyvinyl alcohol (PVA) greater than 3.5, and wherein the flavorant is not present in the encapsulated dye particle, wherein the flavor ingredients have Molecular Weight from 120 to 400 and the dentifrice composition exhibits a color change after a period of 30 to 90 seconds upon usage.

2. The color-changing dentifrice composition according to claim 1, wherein the flavor ingredients are selected from the group consisting of thymol, menthol, caprylic triglyceride, carvone, menthone, g-undecalactone, and combinations thereof.

3. The color-changing dentifrice composition according to claim 1, wherein the encapsulated dye particle has an average particle size of 100 to 2000 microns.

4. The color-changing dentifrice composition according to claim 1, wherein the binder consists of HPMC and PVA.

5. The color-changing dentifrice composition according to claim 1, further comprising active ingredients selected from a fluoride ion source and a metal ion source.

6. The color-changing dentifrice composition according to claim 5, wherein the metal ion source comprises stannous ion source, zinc ion source, and combinations thereof.

7. The color-changing dentifrice composition according to claim 1, further comprising one or more ingredients selected from the group consisting of orally acceptable carriers, abrasives, binders, humectant, surfactant, and combinations thereof.

8. A method of using the color-changing dentifrice composition according to claim 1 for providing visible color-changing experience to a user, the method comprising the step of brushing teeth with the dentifrice composition for more than 1 minute.

9. The color-changing dentifrice composition of claim 1, wherein the coating layer further comprises a filler selected from glucose, mannitol, sorbitol, fructose, lactose, and combinations thereof.

10. The color-changing dentifrice composition of claim 1, wherein the encapsulated dye particle consists essentially of about 1% to 5% of a dye, about 1% to 5% of HPMC, about 1% to 5% of PVA, about 20% to 30% of titanium dioxide, and about 40%-50% of mannitol, by weight of the encapsulated dye particle.

* * * * *